United States Patent
Bender et al.

(10) Patent No.: US 9,422,208 B2
(45) Date of Patent: Aug. 23, 2016

(54) TREATMENT OF AROMATIC HYDROCARBON STREAM

(71) Applicant: ExxonMobil Chemical Patents Inc., Baytown, TX (US)

(72) Inventors: Timothy P. Bender, Houston, TX (US); Chong Jhoo Wang, Singapore (SG); Glenn A. Heeter, The Woodlands, TX (US); Dana L. Pilliod, League City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 295 days.

(21) Appl. No.: 14/221,764

(22) Filed: Mar. 21, 2014

(65) Prior Publication Data

US 2014/0336436 A1    Nov. 13, 2014

Related U.S. Application Data

(60) Provisional application No. 61/820,286, filed on May 7, 2013.

(51) Int. Cl.
| | | |
|---|---|---|
| *C07C 7/13* | (2006.01) | |
| *C07C 7/14* | (2006.01) | |
| *C07C 2/86* | (2006.01) | |

(52) U.S. Cl.
CPC ............ *C07C 2/864* (2013.01); *C07C 2/865* (2013.01); *C07C 7/13* (2013.01); *C07C 7/14* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 3,409,691 | A | 11/1968 | Small |
| 4,064,042 | A | 12/1977 | Kunin |
| 5,218,132 | A | 6/1993 | Mobbs et al. |
| 6,368,496 | B1 | 4/2002 | Brown et al. |
| 6,555,611 | B2 | 4/2003 | Tachifuji et al. |
| 7,517,824 | B2 | 4/2009 | Brown et al. |
| 7,731,839 | B2 | 6/2010 | Brown et al. |
| 7,744,750 | B2 | 6/2010 | Brown et al. |
| 8,048,295 | B2 | 11/2011 | Brown et al. |
| 8,057,664 | B2 | 11/2011 | Brown et al. |
| 8,216,450 | B2 | 7/2012 | Brown |
| 8,227,654 | B2 | 7/2012 | Kinn et al. |
| 8,252,967 | B2 | 8/2012 | Hagemeister et al. |
| 8,329,971 | B2 | 12/2012 | Brown et al. |
| 8,344,200 | B2 | 1/2013 | Brown |
| 2007/0112240 | A1 | 5/2007 | Brown et al. |
| 2012/0316375 | A1 | 12/2012 | Zheng et al. |
| 2013/0253245 | A1 | 9/2013 | Zheng et al. |
| 2013/0324780 | A1 | 12/2013 | Ou et al. |
| 2014/0142361 | A1* | 5/2014 | Gaab ................ C07C 1/20 585/640 |

FOREIGN PATENT DOCUMENTS

| | | |
|---|---|---|
| CN | 1253937 | 5/2000 |
| JP | 5639025 | 4/1981 |
| JP | 7215901 | 8/1995 |

* cited by examiner

*Primary Examiner* — Tam M Nguyen

(57) ABSTRACT

The invention is directed to a process of contacting at least one zeolite, selected from the MWW family of zeolites, with an aromatic hydrocarbon stream in a system comprising at least one reactor containing the at least one zeolite, wherein the conditions in the reactor are adjusted in response to at least one measurement of the system so as to preferentially increase oxygenate removal or to preferentially increase olefin removal.

12 Claims, 3 Drawing Sheets

TREATMENT OF AROMATIC HYDROCARBON STREAM

CROSS REFERENCE TO RELATED APPLICATIONS

This application claims priority to and the benefit of U.S. Provisional Application No. 61/820,286, filed on May 7, 2013, the disclosure of which is incorporated herein by reference in its entirety.

FIELD OF THE INVENTION

The invention relates to the treatment of aromatic hydrocarbon streams to remove oxygenates and olefins.

BACKGROUND OF THE INVENTION

Aromatic streams, which may comprise one or more of benzene, toluene and xylenes (BTX), are used as feedstocks in various petrochemical processes. By way of example, paraxylene obtained from such streams are useful in the production of polyester fibers and films. It is well-known that such streams, derived from processes such as naphtha reforming and thermal cracking (pyrolysis), generally contain undesirable hydrocarbon contaminants including mono-olefins, dienes, styrenes and heavy aromatic compounds such as anthracenes, and that these contaminants must be removed before subsequent processing of the aromatic streams. Zeolites including those from the MWW family of zeolites can remove olefinic compounds from such aromatic streams at least in part by alkylating aromatic compounds with the olefins to form heavy aromatics (C9+ aromatic hydrocarbons) that can, in turn, be removed easily, for instance, by fractionation. See, for example, U.S. Pat. Nos. 6,368,496; 7,517,824; 7,731,839; 7,744,750; 8,048,295; 8,057,664; 8,216,450; 8,227,654; 8,329,971; and 8,344,200.

Less well-known is that in the production of paraxylene by contact of toluene and/or benzene with an alkylating agent such as methanol and/or dimethylether, in the presence of solid acid catalysts, impurities such as oxygenates are produced in side reactions. The product of such alkylation reaction is typically a paraxylene-rich aromatic hydrocarbon stream. The term paraxylene-rich (or "para-rich") means that paraxylene is present in amounts greater than equilibrium amounts, based on total xylenes, for instance greater than 23 mol %. This is a highly valuable feedstream, because paraxylene is much more valuable relative to its isomers. Since many of the known methods of purification of aromatic feedstreams have the drawback of isomerizing xylenes, and isomerization of a paraxylene-rich aromatic hydrocarbon stream towards equilibrium concentration is completely antithetical to the whole purpose of such alkylation reactions, purification of such product streams is any area of intense research.

In this regard U.S. Pat. No. 8,252,967 teaches such oxygenates may be removed from the aromatic hydrocarbon product of the aforementioned alkylation reaction by use of crystallization technology.

In U.S. Patent Publication No. 2012-0316375 the concentration of phenolic impurities in a xylene stream produced by the aforementioned alkylation reaction can be reduced to trace levels, such as below 0.1 ppmw, by one or more washing treatments with an aqueous solution of a base (caustic).

U.S. Patent Publication No. 2013-0253245 is directed to a process including the aforementioned alkylation reaction, the improvement comprising: (a) determining the amount of at least one oxygenate co-produced in the paraxylene-enriched product; (b) separating said product into separate streams including: (i) one or more streams comprising said unreacted components and co-produced oxygenates; (ii) at least one stream comprising paraxylene; (iii) at least one stream comprising C9+ aromatics, if present; (iv) at least one stream comprising light gases, if present; (c) recycling at least one stream selected from unreacted components and co-produced oxygenates, whereby said at least one of these recycled streams combines with the alkylation reactor feed; (d) determining the amount of said at least one oxygenate in said feed, including said recycle; (e) controlling reactor conditions, step (b) and step (c) so that the amount determined in step (a) is less than or equal to the amount determined in step (d).

Recently there has been described a process for the purification of an aromatic hydrocarbon stream containing phenol and greater than equilibrium amounts of paraxylene, comprising contact of said aromatic hydrocarbon stream with an adsorbent selective for the absorption of phenol relative to xylenes, to provide a product stream having lower concentration of phenol than said aromatic hydrocarbon stream. Suitable materials used to remove phenol from the process stream include alumina, silica, molecular sieves, zeolites, basic organic resins, and mixtures thereof. (U.S. Patent Publication No. 2013-0324780.)

Other relevant prior art includes U.S. Pat. No. 6,555,611, teaching an absorbent for absorbing aromatic hydroxyl compounds, said absorbent comprising composite metal oxide solid solution particles or hydrotalcite-like composite metal hydroxide particles; JP 5639025A, teaching removal of phenols from organic matter by contact with a polyvinyl pyridine resin; CN 1253937A, teaching using silica gel to remove phenol-like compounds from styrene monomers; U.S. Pat. No. 3,409,691, teaching removal of phenol by the use of macroporous ion exchange resin; U.S. Pat. No. 4,064,042, teaching separating an organic component such as phenol from blood by contact with a macroporous synthetic polymer; U.S. Pat. No. 5,218,132, teaching removal of aromatic impurities such as phenol by contact with a material including a smectite mineral; and JP 7215901A, teaching contact of a phenol-containing non-aqueous solvent with an acrylic weak basic ion exchange resin.

There are other sources of oxygenate impurities in xylene feedstocks. For instance, such feedstocks often contact oxygen during transport by ships and may contain unacceptably high levels of oxygenated species that could potentially disrupt downstream processing, for example, poisoning of adsorptive separation units such as Parex™ and Eluxyl™ adsorptive separation units, as well as poisoning of catalysts in the several steps required to convert paraxylene into polyesters and other useful derivatives.

Despite a plethora of means to purify various aromatic hydrocarbon streams comprising xylenes, the industry is not satisfied with the results and research into new methods is intense. There is still a need, specifically, for a simple and effective way of purifying paraxylene-rich aromatic hydrocarbon streams to remove impurities including olefins and oxygenates.

SUMMARY OF THE INVENTION

The present inventors have surprisingly discovered that the use of one or more zeolites from the MWW family of zeolites is effective in removing olefin and oxygenate impurities from aromatic hydrocarbon feedstreams containing xylenes with little or no loss of paraxylene, and furthermore that lower temperatures improve the removal of oxygenate removal whereas higher temperatures improve olefin removal.

The invention is directed to the use of at least one zeolite selected from the MWW family of zeolites to remove both olefinic impurities and oxygenate impurities from aromatic hydrocarbon streams comprising paraxylene, particularly paraxylene-enriched aromatic hydrocarbon streams. In one embodiment, at least one zeolite, selected from the MWW family of zeolites, is contacted with an aromatic hydrocarbon stream in a system comprising at least one reactor containing the at least one zeolite. The conditions in the reactor, such as the temperature or space velocity of the aromatic hydrocarbon stream or the temperature of the zeolite, are adjusted in response to at least one measurement of the system, which may be correlated with oxygenate or olefin concentration, so as to preferentially increase oxygenate removal or to preferentially increase olefin removal.

It is an object of the invention to provide a simple but elegant method of removing impurities from an aromatic hydrocarbon stream, particularly an aromatic hydrocarbon stream comprising paraxylene in greater than equilibrium concentration.

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION OF THE INVENTION

Figure 1:
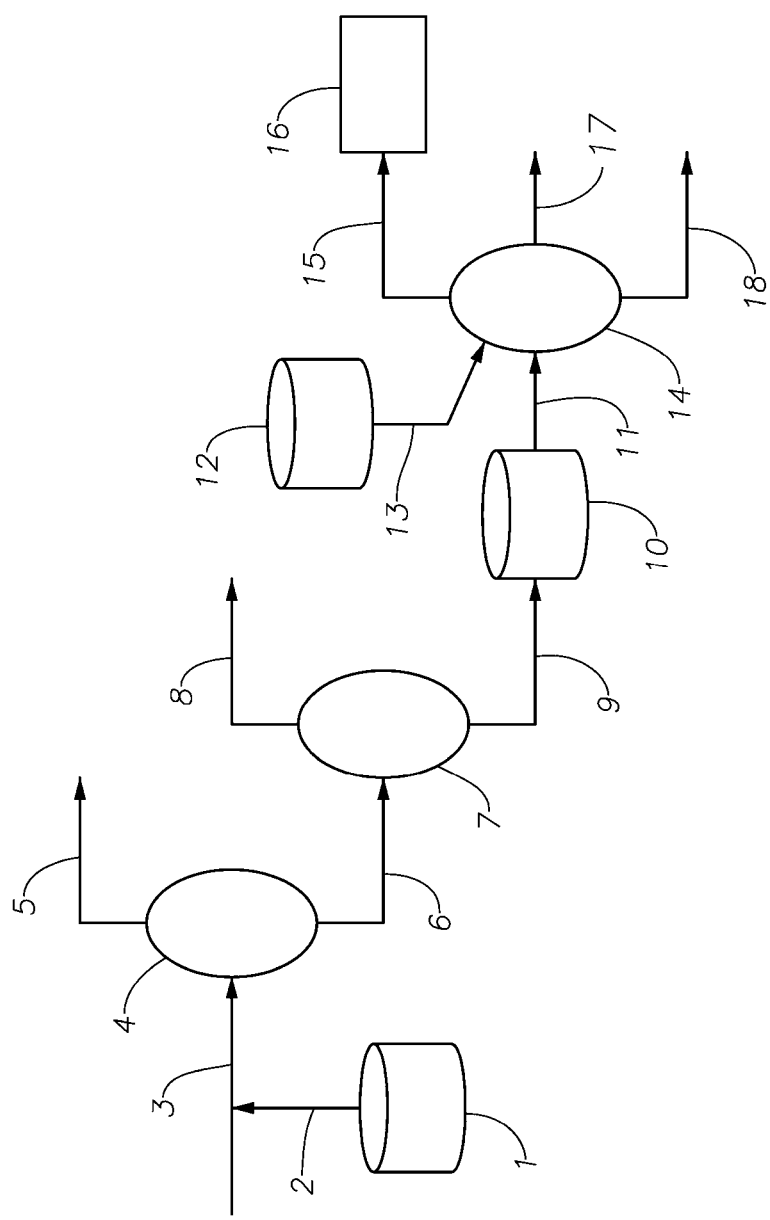
FIG. 1 illustrates schematically a system using the present invention.

According to the invention, an aromatic hydrocarbon stream comprising paraxylene, olefins, and oxygenates, is contacted with at least one zeolite of the MWW family of molecular sieves under conditions effective to remove at least a portion of the olefin and oxygenates therein. The conditions of contact, e.g., space velocity and/or temperature, can be modified or adjusted (e.g., space velocity increased or decreased and/or temperature increased or decreased) so that the amount of olefins removed can be increased and/or the amount of oxygenates removed can be increased.

The zeolite selected from the MWW family of molecular sieves includes at least one of MCM-22, MCM-36, MCM-49, MCM-56, and EMM-10 molecular sieves, and in embodiments can be used in combination with a clay such as Engelhard F-24, Filtrol 24, Filtrol 25, and Filtrol 62 clays, Attapulgus clay and Tonsil clay. The molecular sieves have been described in numerous patents and publications, such as U.S. Pat. No. 4,954,325; U.S. Pat. No. 5,229,341; U.S. Pat. No. 5,236,575; and U.S. Pat. No. 5,362,697; and the clays are likewise well-known. Any of these are commercially available. When used in combination with a clay, the zeolite and clay may be mixed in all proportions, such as 10:90 to 90:10, or they may be packed serially (e.g., first clay and then zeolite, or vice versa, with minimal to no mixing or with spacers to further minimize mixing) or they may be housed in separate reactors and arrayed serially, or a combination thereof. Hydrogen gas may be present in the reactor, either by introduction, intermittently or continuously, or from the aromatic feedstream to the reactor, or a combination thereof.

The aromatic hydrocarbon streams contacting the at least one zeolite are those comprising paraxylene and are selected from: (a) imported aromatic hydrocarbon streams that are subject to exposure to an oxygen-containing environment at some point in processing; (b) product steams from xylene production involving transalkylation, isomerization, alkylation, extraction, reforming, disproportionation, and mixtures thereof; or (c) a combination of such feedstreams. "Imported" means aromatic hydrocarbon streams which are transported by ship, train, pipeline, and the like, which may involve interstate or international shipments. In preferred embodiments, the aromatic hydrocarbon streams comprising paraxylene are paraxylene-rich, i.e., having paraxylene in the amount of greater than 23 mol %, relative to total xylene concentration. In the case of an imported aromatic hydrocarbon feedstream, the paraxylene-rich feedstream may be one obtained from a crystallization process or adsorptive separation process.

The aromatic hydrocarbon streams that contact the at least one zeolite may be derived from an alkylation reaction, such as that disclosed in U.S. Pat. No. 6,504,072 or U.S. Patent Publication No. 2013-0165724, and references cited therein, in which an alkylating agent such as methanol and/or dimethyl ether (DME) is contacted with benzene and/or toluene in the presence of an acid active molecular sieve catalyst in an alkylation reactor. The catalyst and alkylation reactor conditions utilized are effective to produce a product comprising paraxylene in greater than equilibrium amounts (i.e., greater than 23 mol %, relative to total xylenes). Co-produced with the paraxylene are oxygenates such as phenol, non-aromatic hydrocarbons including olefins such as styrene, optionally C9+ aromatic hydrocarbons, and optionally light gases. Unreacted components, including the alkylating agent (methanol or DME), water, benzene and/or toluene, may also be present in the product stream. The product of the alkylation reactor may be separated, such as by fractionation, into one or more constituent parts, and at least one of the constituent parts is contacted by at least one zeolite under conditions effective to reduce the level of oxygenates and olefins, if present, in such constituent parts.

In those embodiments in which the aromatic hydrocarbon feedstream is obtained by the aforementioned alkylation reaction, the invention is a process comprising: (a) optionally separating the product into separate streams, at least a portion of at least one of which is recycled, the separate streams selected from (i) one or more streams comprising unreacted components, (ii) one or more streams comprising oxygenates; (iii) one or more streams comprising olefins; (iv) at least one stream comprising paraxylene; (v) at least one stream comprising C9+ aromatics, if present; (vi) at least one stream comprising light gases, if present; (b) measuring the concentration of at least one oxygenate and/or at least one olefin in the paraxylene product and/or one or more of said separate streams; (c) measuring the concentration of said at least one oxygenate and/or at least one olefin in said the feed to said alkylation reaction, optionally wherein said feed includes said recycle; (d) contacting at least one of (i) said product, (ii) said separate stream, where present, (iii) at least one recycle, where present; (iv) at least one or more streams comprising olefins; (v) at least one or more streams comprising oxygenates, where present; with at least one zeolite selected from the MWW family of zeolites in a reactor under conditions effective to reduce the level of oxygenates and/or olefins, if present; and (e) adjusting the alkylation reactor conditions, and/or conditions in the reactor comprising the at least one zeolite so as to increase the amount of olefin removed the amount of oxygenate removed in step (d).

Step (d), in which the at least one zeolite is contacted with the aromatic hydrocarbon stream, occurs in a system comprising at least one reactor containing the at least one zeolite. In step (e), at least one condition, such as the temperature or space velocity of the aromatic hydrocarbon stream and/or the temperature of the zeolite, in the reactor are adjusted in response to at least one measurement of the system so as to preferentially increase oxygenate removal or to preferentially increase olefin removal. The measurement may be correlated with the concentration of at least one oxygenate or olefin at one or more locations in the system. In preferred embodiments, step (d) occurs in at least two reactors containing the at least one zeolite independently selected from the MWW family of zeolites, and in step (e), the conditions in each reactor are individually adjusted in response to at least one measurement of the system so as to preferentially increase oxygenate removal or to preferentially increase olefin removal in each individual reactor or to increase the total amount of olefins and oxygenates removed from the product.

The inventors have determined that lowering the temperature of the aromatic hydrocarbon solution, which can readily be accomplished by one of ordinary skill in the art in possession of the present disclosure, prior to contact with the zeolite will cause more organic oxygenates to be adsorbed. This phenomenon allows a convenient method of desorbing the oxygenates—by increasing the temperature—in a regeneration procedure which conveniently would utilize a non-paraxylene-rich stream. Additionally, raising the temperature of the aromatic hydrocarbon solution prior to contact with the zeolite increases the removal of olefin. Accordingly, the removal of olefin and oxygenate can be managed simply by adjustment of temperature. Conveniently, then, it is advantageous to have a series of two or more reactors, sequentially managed by adjustment of temperatures to selectively remove one or the other of olefin and oxygenate, respectively.

In embodiments, downstream of the oxygenate and/or olefin removal according to the claimed invention described herein, there is at least one process selected from: (i) a process comprising the isolation of at least one of the isomers of xylene, for example, paraxylene, such as crystallization or adsorptive separation, the latter represented, by way of example, by a Parex™ unit or an Eluxyl™ unit, optionally further comprising liquid or vapor phase isomerization of the filtrate from said crystallization process or the raffinate from said adsorption process; and/or (ii) a manufacturing process comprising the production of polyester or a precursor thereof, starting from paraxylene; and/or (iii) the isomerization of a non-equilibrium xylenes mixture to equilibrium, such as by vapor-phase or liquid-phase isomerization.

The present invention may be better understood by reference to the figures and the example set forth below, which are intended to be illustrative and representative and not limiting of the present invention.

In FIG. 1, a xylene-containing feedstream 3, such as a paraxylene-rich stream from an alkylation reactor or an equilibrium xylene stream from a steam cracker, reforming unit, and the like (or combination thereof), is passed to separation device 4 of the type known in the art, such as one or more fractionating towers. This feedstream may be mixed with a source of paraxylene which has been contaminated with oxygen during shipment, such as by pipeline, ship, train, and the like, said source represented by "storage tank" 1 and added to conduit 3 via conduit 2. The one or more fractionating tower (s) yield light ends (e.g., aliphatics such as butane and pentane), water, and oxygen as overheads 5 and stream 6 comprising C6+ aromatic hydrocarbons (e.g., BTX materials and C9+ aromatic hydrocarbons) as bottoms, which is passed to one or more separation devices 7 e.g., one or more fractionator(s) wherein benzene and toluene (C7− aromatic hydrocarbons) are removed via overhead 8, yielding C8+ aromatic hydrocarbons as a bottom product 9. The apparatus depicted by unit 10 represents one or more reactors comprising at least one or more zeolites selected from the MWW family, and which is the concern of the present invention, along with one or more measuring devices and heating and/or cooling devices. It will be understood that 10, and more generally, FIG. 1 does not show valves, heat exchangers, and other equipment, such as one or more computers, measuring devices, heating and cooling devices, and the like, which would be apparent to one of ordinary skill in the art in possession of the present disclosure, for convenience of view.

The effluent 11 from apparatus 10, comprising an aromatic hydrocarbon stream having a lower concentration of at least one oxygenate and/or at least one olefin than the aromatic hydrocarbon stream in conduit 9, is then passed to xylene column 14, which may be of the conventional type known in the art, to provide a bottom cut 18 comprising heavies (C9+ aromatic hydrocarbons) and xylenes product 15, which is passed to device 16, representing one or more devices associated with crystallizer technology or adsorptive separation technology, per se well known in the art. Preferably the device is a Parex™ unit or Eluxyl™ unit, which yields purified paraxylene and raffinate, neither stream shown for convenience of view.

In a preferred embodiment of the system illustrated in FIG. 1, there is a "source" represented by apparatus 12, of C8+ aromatic hydrocarbon product, which may be from the raffinate, in the case of device 16 being an adsorptive separation unit, or filtrate, in the case of device 16 being crystallizer technology, which has been isomerized by an apparatus, not shown, which may be vapor phase or liquid phase isomerization device(s) or a combination thereof. This source is preferably fed via conduit 13 to the top section of fractionator 17.

Figure 2:
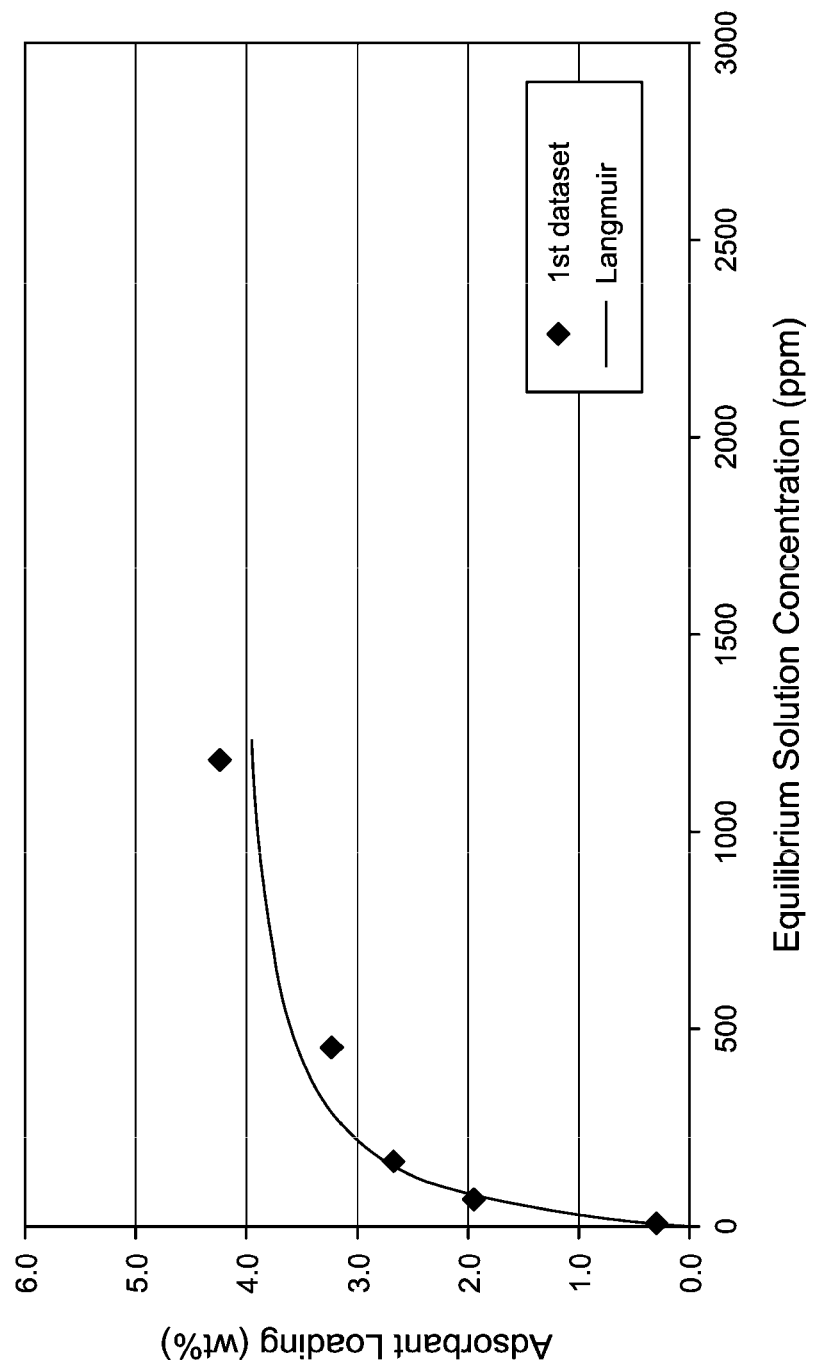
FIGS. 2 and 3 set forth data from experiments illustrating the adsorption of certain oxygenates on zeolites from the MWW family of molecular sieves.
Figure 3:
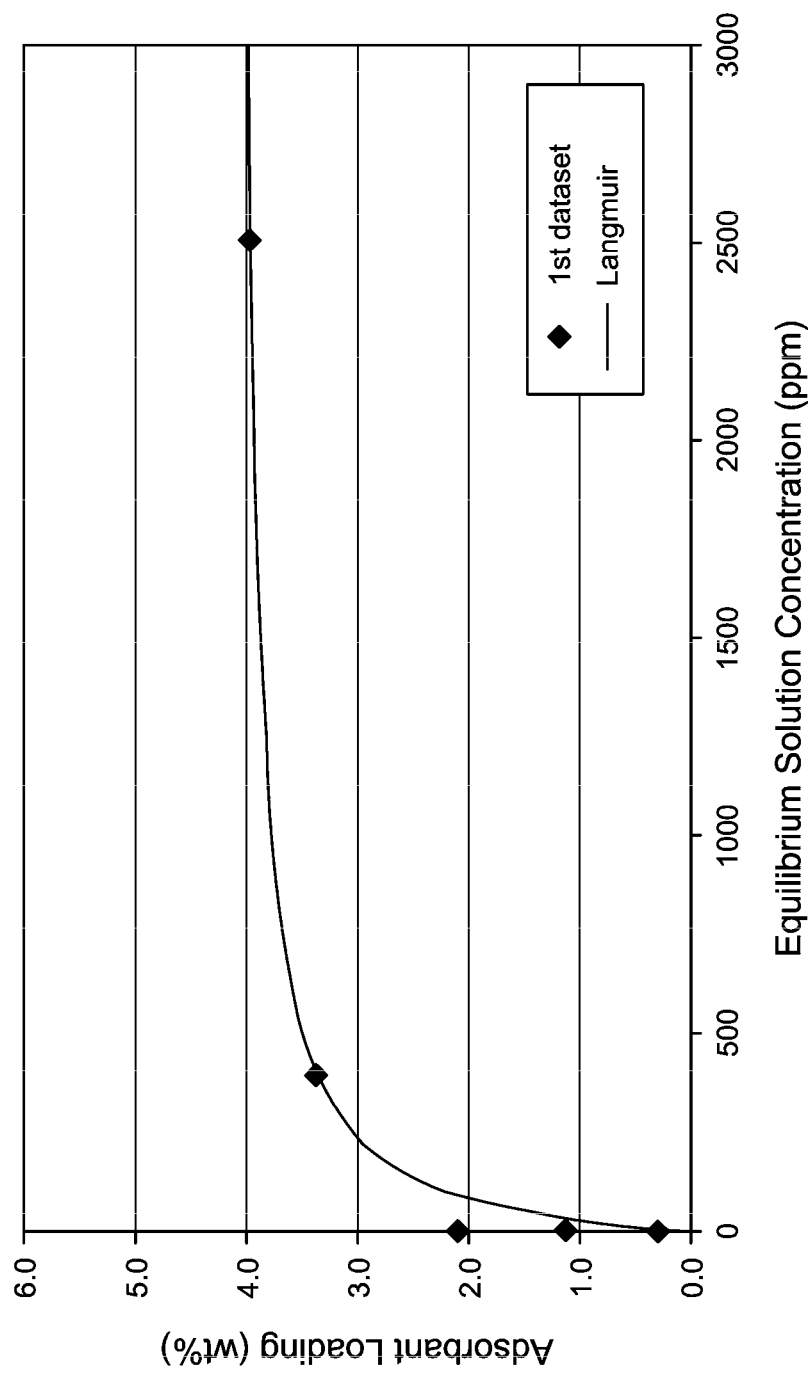

It has been experimentally demonstrated that the use of a zeolite from the MWW family is effective in removing oxygenates, as shown in FIGS. 2 and 3.

In FIG. 2, the capacity of MCM-22 to adsorb acetophenone from a paraxylene-rich stream produced by an alkylation reaction as discussed hereinabove is shown. On the y-axis further is the adsorbant loading, i.e., the capacity of the zeolite to adsorb the oxygenate (wt %) relative to the total weight of zeolite and adsorbant from a solution spiked with various concentrations of acetophenone, as shown on the x-axis. 5 data points are shown by the diamonds; the curve is what is predicted by Langmuir equation.

FIG. 3 shows the identical experiments performed with solutions spiked with various concentrations of m-tolualdehyde.

The invention has been described above with reference to numerous embodiments and specific examples. Many variations will suggest themselves to those skilled in this art in light of the above detailed description. All such obvious variations are within the full intended scope of the appended claims.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A process comprising contacting an aromatic hydrocarbon stream comprising xylenes, olefins, and oxygenates, in at least two reactors containing at least one zeolite independently selected from the MWW family of zeolites, to produce a product stream from said reactor,
   wherein at least one condition of contacting in each reactor is individually adjusted in response to at least one measurement of a system comprising said zeolite, said aromatic hydrocarbon stream, said reactor, and said product stream, so as to preferentially increase oxygenate removal or to preferentially increase olefin removal from said aromatic hydrocarbon stream in each individual reactor,
   wherein said at least one condition of contacting is selected from the temperature and/or space velocity of said aromatic hydrocarbon stream, the temperature of said zeolite, and combinations thereof.

2. The process of claim 1, wherein said measurement is correlated with the concentration of at least one oxygenate or olefin at one or more than one location in said system.

3. The process of claim 1, wherein hydrogen gas is present in said at least two reactors.

4. The process of claim 1, wherein hydrogen gas is not present in said at least two reactors.

5. The process of claim 3, wherein hydrogen gas is intermittently supplied to said at least two reactors.

6. The process of claim 1, wherein the aromatic hydrocarbon stream is selected from at least one of (a) imported aromatic hydrocarbon streams that are subject to exposure to an oxygen-containing environment at some point in processing; (b) product steams from xylene production involving transalkylation, isomerization, alkylation, extraction, reforming, disproportionation, and mixtures thereof.

7. The process of claim 1, wherein downstream of said reactors there is at least one process selected from: (i) a process comprising the isolation of at least one of the isomers of xylene, preferably crystallization or adsorptive separation; (ii) a manufacturing process comprising the production of polyester or a precursor thereof, starting from paraxylene; and/or (iii) the isomerization of a non-equilibrium xylenes mixture to equilibrium, such as by vapor-phase or liquid-phase isomerization.

8. The process of claim 1, wherein the aromatic hydrocarbon stream that contacts the at least one zeolite selected from the MWW family of zeolites is derived from an alkylation reaction comprising contact of an alkylating agent including methanol and/or dimethylether (DME) with benzene and/or toluene in the presence of an acid active molecular sieve catalyst in an alkylation reactor wherein said catalyst and alkylation reactor conditions are effective to produce an alkylation reactor product comprising paraxylene in greater than equilibrium amounts, co-produce oxygenates such as phenol, optionally C9+ aromatic hydrocarbons, non-aromatic hydrocarbons including styrene and optionally light gases, and optionally unreacted components including the alkylation agent (methanol and/or DME), water, benzene and/or toluene.

9. The process of claim 8, wherein the product of the alkylation reactor is separated into one or more constituent parts, and at least one of said constituent parts comprises said paraxylene.

10. The process of claim 8, comprising:
   (a) optionally separating said alkylation reactor product into separate streams, at least a portion of at least one of which is recycled to said alkylation reactor, said separate streams selected from (i) one or more streams comprising unreacted components, (ii) one or more streams comprising oxygenates; (iii) one or more streams comprising olefins; (iv) at least one stream comprising paraxylene; (v) at least one stream comprising C9+ aromatics, if present; (vi) at least one stream comprising light gases, if present;
   (b) measuring the concentration of at least one oxygenate and/or at least one olefin in the paraxylene product and/or one or more of said separate streams;
   (c) measuring the concentration of said at least one oxygenate and/or at least one olefin in said the feed to said alkylation reaction, optionally wherein said feed includes said recycle;
   (d) contacting at least one of (i) said product, (ii) at least one of said separate streams, (iii) at least one recycle, where present; (iv) at least one or more streams comprising olefins; (v) at least one or more streams comprising oxygenates, where present; with at least one zeolite independently selected from the MWW family of zeolites in at least two reactors under conditions effective to reduce the level of oxygenates and/or olefins, if present; and
   (e) adjusting at least one of the temperature and/or space velocity of said aromatic hydrocarbon stream, the temperature of said zeolite, or combinations thereof in at least one of said at least two reactors so as to increase the amount of olefin removed and/or increase the amount of oxygenate removed in step (d).

11. The process of claim 1, wherein the at least one zeolite from the MWW family of molecular sieves is selected from MCM-22, MCM-36, MCM-49, MCM-56, and EMM-10.

12. The process of claim 1, wherein the at least one zeolite is used mixed with or in series with a clay.

* * * * *